United States Patent [19]

Tamura et al.

[11] Patent Number: 5,858,936
[45] Date of Patent: Jan. 12, 1999

[54] DETERGENT COMPOSITION

[75] Inventors: Yoshinori Tamura; Yasuhiro Doi; Keiko Hasebe; Masafumi Shonaka; Tadashi Moriyama; Yuichi Hioki; Hiroshi Sonohara, all of Wakayama, Japan

[73] Assignee: Kao Corporation, Tokyo, Japan

[21] Appl. No.: 821,302

[22] Filed: Mar. 20, 1997

[30] Foreign Application Priority Data

Apr. 5, 1996 [JP] Japan ................................ 8-083719
Nov. 20, 1996 [JP] Japan ................................ 8-309186

[51] Int. Cl.$^6$ ........................................... C11D 1/86
[52] U.S. Cl. ........................ 510/131; 510/384; 510/504
[58] Field of Search ................................. 510/131, 135, 510/159, 383, 384, 414, 427, 434, 476, 479, 490, 501, 503, 504

[56] References Cited

U.S. PATENT DOCUMENTS 4,354,952 10/1982 Riedhammer et al. ................. 252/106
4,543,205 9/1985 Contamin ............................. 252/546
5,585,341 12/1996 Van Eenam ............................ 510/365

FOREIGN PATENT DOCUMENTS

141732 A2 5/1985 European Pat. Off. .
642782 A2 3/1995 European Pat. Off. .
91/00336 1/1991 WIPO .
96/06595 3/1996 WIPO .

*Primary Examiner*—Paul Lieberman
*Assistant Examiner*—John R. Hardee
*Attorney, Agent, or Firm*—Oblon, Spivak, McClelland, Maier & Neustadt, P.C.

[57] ABSTRACT

Described is a detergent composition comprising (A) a sulfate ester surfactant, (B) at least one surfactant selected from amphoteric surfactants, amine oxide surfactants, alkanol amide surfactants and amide amino-acid surfactants, (C) a cationic bactericide and (D) a metal chelating agent, the weight ratio of said (A) to (B) being 1–50 and the content of said (C) being 0.2 wt. % to 5 wt. %.

The detergent composition according to the present invention has excellent detergency, foamability and foam durability and at the same time, has high bactericidal effects because it can be mixed stably with a cationic bactericide.

13 Claims, No Drawings

DETERGENT COMPOSITION

BACKGROUND OF THE INVENTION

1. Field of the Invention

This invention relates to a detergent composition. More specifically, the present invention pertains to a detergent composition which has excellent detergency, foamability and foam durability and besides, which can impart sufficient anti-dandruff properties to the scalp and antipruritic and deodorizing effects to the body and skin because the composition can be mixed with a cationic bactericide stably, thereby exhibiting high bactericidal effects.

2. Description of the Related Art

For a major ingredient of many detergents, particularly hair detergents, a polyoxyethylene alkyl or alkenyl ether sulfate ester salt has been used conventionally as an anionic surfactant because it can impart excellent detergency and foaming power to the detergent. Besides, a number of detergents having bactericidal effects have been studied and those containing, as a bactericide, a cationic bactericide are known. The addition of such a cationic bactericide to a detergent which contains, as a major ingredient, an anionic surfactant, however, forms a complex therebetween and causes difficulty in the incorporation, thereby disturbing the sufficient exhibition of the bactericidal effects.

For the prevention of such lowering in the activity, it is the common practice to coat the cationic bactericide with a polymeric nonionic surfactant or pH sensitive polymer or to add the cationic bactericide in a great excess. But, the former method lowers the activity of the cationic bactericide, while the latter method using an excess amount is not preferred economically.

In addition, known is a method (Japanese Patent Application Laid-Open No. 122893/1994) in which, even in an anionic surfactant, the effects of a cationic bactericide can be exhibited by the addition of a chelating agent. When a sulfate ester surfactant is used as a major ingredient for the anionic surfactant, however, the above method is accompanied with the problem that bactericidal effects cannot be exhibited fully, though depending on the kind of the bacteria because a bactericidal spectrum is limited and a wide bactericidal spectrum cannot be attained.

SUMMARY OF THE INVENTION

Accordingly, an object of the present invention is to provide a detergent composition which has excellent detergency, foamability and foam durability and besides, can impart sufficient anti-dandruff properties and antipruritic and deodorizing effects to the scalp or body because the composition can be mixed stably with a cationic bactericide, thereby exhibiting high bactericidal effects and wide bactericidal spectrum.

The present invention therefore provides a detergent composition comprising the following components (A), (B), (C) and (D):

(A) a sulfate ester surfactant represented by the following formula (1):

$$R^1O-(CH_2CH_2O)_n-SO_3M^1 \quad (1)$$

wherein $R^1$ represents a linear or branched $C_{8-20}$ alkyl or alkenyl group, n stands for an integer of 0–10 on average, and $M^1$ represents an alkali metal atom, alkaline earth metal atom, ammonium salt, alkyl ammonium salt or alkanol ammonium salt;

(B) at least one surfactant selected from the group consisting of amphoteric surfactants, amine oxide surfactants, alkanol amide surfactants and amide amino-acid surfactants;

(C) at least one cationic bactericide selected from the group consisting of cationic bactericides represented by the below-described formulas (2), (3), (4) and (5), respectively and polyhexamethylene biguanide:

wherein $R^2$ and $R^3$ are the same or different and each independently represents a long-chain alkyl group, long-chain alkenyl group or long-chain hydroxyalkyl group, said $R^2$ and $R^3$ each having 6–14 carbon atoms and totally having 16–26 carbon atoms, $R^4$ and $R^5$ are the same or different and each independently represents a $C_{1-3}$ alkyl or hydroxyalkyl group or a polyoxyethylene group having an average addition moles of 10 or lower, and $Z^1$ represents a halogen atom, an amino acid, a fatty acid, an anionic residue of a phosphate ester, phosphonate ester, sulfonate ester or sulfate ester having a linear or branched $C_{1-30}$ alkyl or alkenyl group, or an anionic oligomer or polymer containing a formalin condensate of a sulfonated polycyclic aromatic compound which may contain styrenesulfonic acid having a polymerization degree of at least 3 or may contain as a substituent a hydrocarbon group;

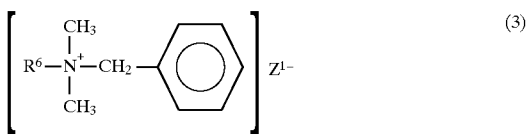

wherein $R^6$ represents a $C_{8-14}$ hydrocarbon group or a group represented by the following formula:

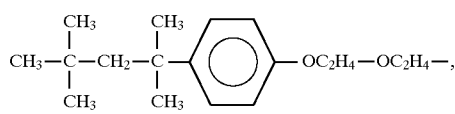

$Z^1$ represents a halogen atom, an amino acid, a fatty acid, an anionic residue of a phosphate ester, phosphonate ester, sulfonate ester or sulfate ester having a linear or branched $C_{1-30}$ alkyl or alkenyl group, or an anionic oligomer or polymer containing a formalin condensate of a sulfonated polycyclic aromatic compound which may contain styrenesulfonic acid having a polymerization degree of at least 3 or may contain as a substituent a hydrocarbon group;

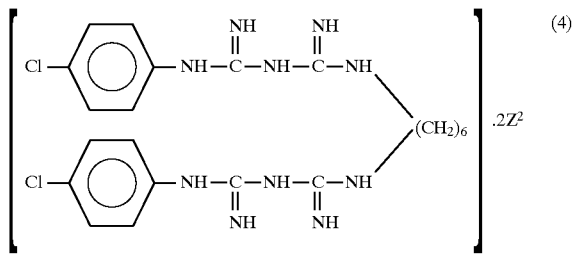

wherein $Z^2$ represents a gluconic acid, acetic acid or hydrochloric acid;

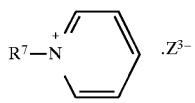

wherein $R^7$ represents a linear or branched $C_{6-18}$ alkyl group, and $Z^3$ represents a halogen atom, an amino acid, a fatty acid, an anionic residue of a phosphate ester, phosphonate ester, sulfonate ester or sulfate ester having a linear or branched $C_{1-30}$ alkyl or alkenyl group, or an anionic oligomer or polymer containing a formalin condensate of a sulfonated polycyclic aromatic compound which may contain styrenesulfonic acid having a polymerization degree of at least 3 or may contain as a substituent a hydrocarbon group; and (D) a metal chelating agent, the weight ratio of the component (A) to the component (B) falling within a range of from 1 to 50 and the content of the component (C) falling within a range of from 0.2 wt. % to 5 wt. %.

The detergent composition according to the present invention has excellent detergency, foamability and foam durability and at the same time, has low irritation. It can be mixed stably with a cationic bactericide and thereby exhibits high bactericidal effects and wide bactericidal spectrum, which makes it possible to impart sufficient anti-dandruff properties to the skin and antipruritic and deodorizing effects to the body and skin.

DETAILED DESCRIPTION OF THE PREFERRED EMBODIMENTS

In the formula (1) which represents the sulfate ester surfactant (A) used in the present invention, linear or branched alkyl or alkenyl group having 10–16 carbon atoms is preferred as $R^1$. As n, the preferred value is 0 to 6 on average from the viewpoints of detergency and foamability, with 0–4 being more preferred and 1–4 being particularly preferred. As $M^1$, a sodium atom, ammonium and triethanol ammonium are particularly preferred in view of solubility.

The sulfate ester surfactant used as the component (A) serves as a major detergent surfactant of the detergent composition of the present invention and it is used in an amount not smaller than 50 wt. % based on the sum of the detergent surfactants. From the viewpoints of detergency, foamability, miscibility with other components or the like, it is preferably added in an amount of 5–50 wt. % (which will hereinafter be indicated as "%", simply), more preferably 7–30%, particularly preferably 8–25%, each based on the total composition.

Examples of the amphoteric surfactant used as the component (B) in the present invention include betaine-type amphoteric surfactants each represented by the following formula (6):

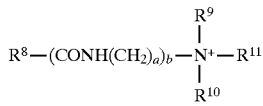

wherein $R^8$ represents a linear or branched $C_{8-22}$ alkyl or alkenyl group, a stands for an integer of 1–4, b stands for 0 or 1, $R^9$ and $R^{10}$ each independently represents a $C_{1-4}$ alkyl group or a group —$(CH_2CH_2O)_dH$ in which d stands for an integer of 1–3 on average, and $R^{11}$ represents a group —$CH_2CH(OH)CH_2SO_3^-$, —$(CH_2)_eSO_3^-$ or —$(CH_2)_fCOO^-$ in which e stands for an integer of 2–5 and f stands for an integer of 1–3.

Among the above-described betaine-type amphoteric surfactants, preferred are a carbobetaine-type amphoteric surfactant represented by the following formula (6a):

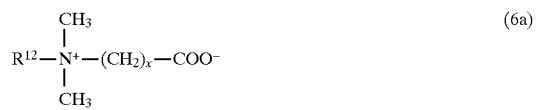

wherein $R^{12}$ represents a linear or branched $C_{8-20}$ alkyl or alkenyl group or a group represented by the formula $R^{13}CONH(CH_2)_y$— in which $R^{13}$ represents a linear or branched $C_{8-20}$ alkyl or alkenyl group and y stands for an integer of 1–5, and x stands for an integer of 1–5; and a sulfobetaine type or hydroxysulfobetaine type amphoteric surfactant represented by the following formula (6b) or (6c):

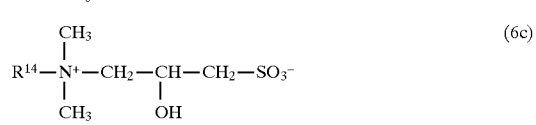

wherein $R^{14}$ represents a linear or branched $C_{8-20}$ alkyl or alkenyl group and X has the same meaning as defined above. More specifically, as $R^{12}$ in the formula (6a), preferred is a linear or branched $C_{8-16}$ alkyl or alkenyl group or a group $R^{13}CONH(CH_2)_3$ in which $R^{13}$ represents a linear or branched $C_{8-16}$ alkyl or alkenyl group; and as X, 1 is preferred. In the formula (6b) or (6c), a linear or branched $C_{8-16}$ alkyl or alkenyl group is preferred as $R^{14}$. Moreover, in the formula (6a), a fatty acid amidopropylbetaine having, as $R^{12}$, a group $R^{13}CONH(CH_2)y$— in which $R^{13}$ represents a linear or branched $C_{8-16}$ alkyl or alkenyl group and y stands for 3 is particularly preferred.

Examples of the amine oxide surfactant used as the component (B) in the present invention include those represented by the following formula (7):

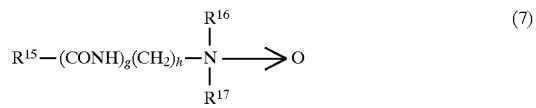

wherein $R^{15}$ represents a linear or branched $C_{8-18}$ alkyl or alkenyl group, $R^{16}$ and $R^{17}$ each independently represents a methyl, ethyl or hydroxyethyl group, g stands for 0 or 1 and h stands for an integer of 0–3.

Among them, those of the formula (7) in which $R^{16}$ and $R^{17}$ are methyl groups at the same time and g and h each stands for 0 are preferred.

Examples of the alkanol amide surfactant used as the component (B) in the present invention include those represented by the following formula (8):

wherein $R^{16}$ represents a linear or branched $C_{7-19}$ alkyl or alkenyl group, p and q each independently represents an integer of 0–10 and at least one of p and q stands for an integer of 1 or greater. Among them, alkanol amide surfactants of the formula (8) in which $R^{16}$ represents a linear or branched $C_{7-15}$ alkyl or alkenyl group, p+q are 1–5, particularly 2, are preferred.

Examples of the amide amino-acid surfactant used as the component (B) in the present invention include those represented by the following formula (9) or (10):

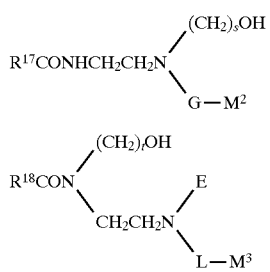

$$R^{17}CONHCH_2CH_2N\diagup^{(CH_2)_sOH}_{\diagdown G-M^2} \quad (9)$$

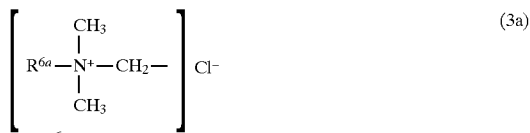

wherein $R^{17}$ and $R^{18}$ each independently represents a linear or branched $C_{7-19}$ alkyl or alkenyl group, s and t each independently stands for an integer of 2–4, G and L each independently represents a group —$CH_2CH(OH)CH_2SO_3$, —$(CH_2)_uSO_3$ or —$(CH_2)_vCOO$ in which u stands for an integer of 2–5 and v stands for an integer of 1–3, E represents a hydrogen atom or a group —L—$M_3$, and $M_2$ and $M_3$ each independently represents a hydrogen atom, an alkali metal, an alkaline earth metal, ammonium or organic ammonium or a mixture thereof.

Specific examples of $M^2$ or $M^3$ include hydrogen, lithium, sodium, potassium, ½ calcium, ½ magnesium, ammonium, monoethanol ammonium, diethanol ammonium, triethanol ammonium, monoisopropanol ammonium, diisopropanol ammonium and triisopropanol ammonium.

The above-described amide amino-acid surfactant is a surfactant available by reacting, for example, 1 mole of an imidazoline derivative with 1–2 moles of monochloroacetic acid or acrylic acid and it was once called as an imidazoline type amphoteric surfactant or imidazolinium betaine. It corresponds to that described in the Fifth edition of the CTFA Dictionary as SODIUM COCOAMPHOACETATE, SODIUM COCOAMPHOPROPIONATE, SODIUM COCOAMPHOHYDROXYROPYLSULFONATE, SODIUM LAUROAMPHOACETATE, SODIUM LAUROAMPHOPROPIONATE or DISODIUM COCOAMPHODIACETATE and is widely known as a trade mark of "Miranol".

At least one surfactant which is a component (B) selected from the group consisting of amphoteric surfactants, amine oxide surfactants, alkanol amide surfactants and amide amino-acid surfactants is added to the composition preferably in an amount of 0.5–10%, more preferably 0.8–10%, particularly preferably 1–8%, most preferably 1–5% based on the whole composition, from the viewpoints of detergency, foamability, bactericidal effects and irritation.

In the detergent composition of the present invention, the weight ratio of (A) to (B) is 1–50, preferably 1–10, more preferably 1–6 and particularly preferably 1–4. When the weight ratio of (A) to (B) exceeds 50, the bactericidal effects of the component (C) cannot be attained easily. When the weight ratio is less than 1, sufficient detergency cannot be attained easily.

As the cationic bactericide which is used as the component (C) in the present invention, employed is at least one bactericide selected from the group consisting of quaternary ammonium salt represented by the formula (2), benzalconium salts or benzethonium salts represented by the formula (3), chlorohexidine salts represented by the formula (4), pyridinium salts represented by the formula (5) and polyhexamethylene biguanides.

Polyhexamethylene biguanides correspond to those described in the 5th edition of International Cosmetic Ingredient Dictionary of CTFA and they are known under the trademark of "Cosmocil" or "Mikrokill".

As $Z^1$ in the formula (2) or (3), a halogen atom is particularly preferred.

Preferred specific examples of the component (C) include benzalkonium chloride, benzethonium chloride, cetylpyridinium chloride, chlorohexidine gluconate, chlorohexidine acetate and chlorohexidine chloride, with benzalconium chloride and benzethonium chloride being particularly preferred. In addition, a benzalkonium-type bactericide represented by the following formula (3a):

$$\left[ R^{6a}-\overset{CH_3}{\underset{CH_3}{\overset{|}{N^+}}}-CH_2- \right] Cl^- \quad (3a)$$

wherein $R^{6a}$ represents a linear or branched $C_{8-14}$ alkyl or alkenyl group, for example, benzalkonium chloride is preferred.

As the component (C), cationic bactericides can be used either singly or in combination. From the viewpoints of bactericidal effects and irritation, the cationic bactericide is added in an amount of 0.2–5%, preferably 0.5–2%, based on the total composition.

No particular limitation is imposed on the metal chelating agent used as the component (D) insofar as it has a chelating ability of a metal ion. Examples include aminopolycarboxylic acid chelating agents, aromatic or aliphatic carboxylic acid chelating agents, amino acid chelating agents, ether polycarboxylic acid chelating agents, phosphonic acid chelating agents such as iminodimethylphosphonic acid (IDP), alkyldiphosphonic acid (ADPA) or 1-hydroxyethane-1,1-diphosphonic acid (DEQUEST™ 2010), hydroxycarboxylic acid chelating agent, phosphoric acid chelating agent, high-molecular electrolyte (including an oligomer electrolyte) chelating agents and dimethyl glyoxime (DG). These chelating agents may be in the form of a free acid or a salt such as sodium salt, potassium salt or ammonium salt. Alternatively, they may be in the form of their hydrolyzable ester derivatives.

Specific examples of the aminopolycarboxylic chelating agent include:

a): compounds represented by the formula $R^{19}N(Y)_2$,
b): compounds represented by the formula $N(Y)_3$,
c): compounds represented by the formula $R^{19}$—N(Y)—$CH_2CH_2$—N(Y)—$R^{19}$,
d): compounds represented by the formula $R_{19}$—N(Y)—$CH_2CH_2$—N(Y)$_2$,
e): compounds represented by the formula $(Y)_2N$—$R^{20}$—N(Y)$_2$, and
f): compounds similar to those described in e) and contain at least 4 Ys, for example, the compound represented by the following formula:

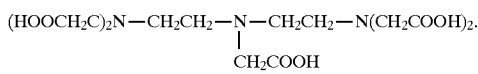

$$(HOOCH_2C)_2N-CH_2CH_2-\underset{\underset{CH_2COOH}{|}}{N}-CH_2CH_2-N(CH_2COOH)_2.$$

In the above formula, Y represents —$CH_2COOH$ or —$CH_2CH_2COOH$, $R^{19}$ represents a hydrogen atom or a group—such as an alkyl group, hydroxyl group or hydroxyalkyl group—which constitutes a known chelating agent and $R^{20}$ represents a group—such as an alkylene group or cycloalkylene group—which constitutes a known chelating agent of the type usable in the present invention.

Representative examples of the aminopolycarboxylic acid chelating agent include ethylene diamine tetraacetic acid (EDTA), cyclohexane diamine tetraacetic acid (CDTA), nitrilotriacetic acid (NTA), iminodiacetic acid (IDA), N-(2-hydroxyethyl)iminodiacetic acid (HIMDA), diethylene triamine pentaacetic acid (DTPA), N-(2-hydroxyethyl)

ethylene diamine triacetic acid (EDTA-OH) and glycol ether diamine tetraacetic acid (GEDTA) and salts thereof.

Examples of the aromatic or aliphatic carboxylic acid chelating agent for use in the present invention include oxalic acid, malonic acid, succinic acid, glutaric acid, adipic acid, itaconic acid, aconitic acid, pyruvic acid, salicylic acid, acetylsalicylic acid, hydroxybenzoic acid, aminobenzoic acid (including anthranylic acid), phthalic acid, trimellitic acid and gallic acid; and salts, methyl esters or ethyl esters of the above-exemplified acid. Examples of the amino acid chelating agent for use in the present invention include glycine, cerin, alanine, lysine, cystine, cysteine, ethionine, tyrosine and methionine, and salts or derivatives thereof.

Examples of the ether polycarboxylic acid chelating agent usable in the present invention include diglycolic acid, compounds represented by the below-described formula and analogous compounds, and salts thereof (ex. sodium salt).

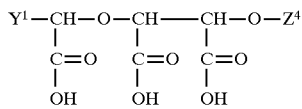

wherein $Y^1$ represents a hydrogen atom, $-CH_2COOH$ or $-COOH$ and $Z^4$ represents a hydrogen atom, $-CH_2COOH$ or

Examples of the hydroxycarboxylic acid chelating agent usable in the present invention include malic acid, citric acid, glycolic acid, gluconic acid, heptoic acid, tartaric acid and lactic acid, and salts thereof. Examples of the phosphoric acid chelating agent usable in the present invention include orthophosphoric acid, pyrophosphoric acid, triphosphoric acid and polyphosphoric acid. Examples of the high-molecular electrolyte (including an oligomer electrolyte) chelating agent usable in the present invention include acrylic acid polymers, maleic anhydride polymers, α-hyroxyacrylic acid polymers and itaconic acid polymers, and copolymers composed of at least two of the component monomer of the above polymers, and epoxysuccinic acid polymers. In the present invention, ascorbic acid, thioglycolic acid, phytic acid, glyoxylic acid and glyoxalic acid, and salts thereof can also be used suitably as a chelating agent.

Preferred examples of the chelating agent used as the component (D) in the present invention include ethylene diamine tetraacetic acid, succinic acid, salicylic acid, oxalic acid, lactic acid, fumaric acid, tartaric acid and 1-hydroxyethane-1,1-diphosphonic acid, and salts thereof.

The chelating agent which is the component (D) is preferably added in an amount of 0.5–5 times, more preferably 1–2 times the mole of the cationic bactericide (C) (the total moles in the case where two or more bactericides are employed). Amounts less than 0.5 time the mole cannot bring about sufficient improving effects on the bactericidal activity.

It is also possible to add an anionic surfactant, which is customarily used in a detergent, to the detergent composition of the present invention within an extent not impairing the advantages of the present invention. Examples of such an anionic surfactant include alkylsulfonate salts, sulfosuccinate esters, α-sulfofatty acid ester salts, α-olefin sulfonate salts, saturated or unsaturated fatty acid salts, phosphoric monoester type surfactants and acylated amino acids.

Furthermore, it is possible to add, to the detergent composition of the present invention, a silicone derivative in an amount within an extent not impairing the advantages of the present invention, more specifically, in an amount of about 0.1–2%. The addition of the silicone resin can bring about good smoothness or stickiness-free feeling. No particular limitation is imposed on the silicone derivative insofar as it is customarily added to a detergent or cosmetic composition. Examples include dimethyl polysiloxane, methylphenyl polysiloxane, polyether-modified silicone, epoxy-modified silicone, alkoxy-modified silicone, amino-modified silicone, fatty-acid-modified silicone and fluorine modified silicone.

It is also possible to add an anti-dandruff in an amount of about 0.1–2% to the detergent composition of the present invention. Exemplary anti-dandruffs include zinc pyrithione, pyroctone olamine (octopirox) and selenium disulfide.

In addition to the above-described components, those generally added to a cosmetic composition, pharmaceutical, food or the like can be added to the detergent composition of the present invention as needed within an extent not impairing the advantages of the present invention. Examples include bactericides other than the cationic bactericide, anti-inflammatories, drug efficacy agents and antiseptics; humectants such as propylene glycol, glycerin, diethylene glycol monoethyl ether, sorbitol or panthenol; colorants such as dye or pigment; pearling agents or chitosan derivatives such as hydroxypropylchitosan; various mixed perfumes; and components described in ENCYCLOPEDIA OF SHMPOO INGREDIENTS (MICELLE PRESS 1985).

The detergent composition of the present invention can be prepared in a manner known per se in the art in the form of a paste, gel or liquid. It is suited as a hair or body detergent and is particularly suited as a hair detergent.

EXAMPLES

The present invention will hereinafter be described more specifically by the following examples. It should however be borne in mind that the present invention will not be limited to or by the following examples. Incidentally, the amount of each component in the examples is indicated using its effective ingredient as a standard.

Example 1

Shampoos having the compositions as shown in Tables 1–3 were prepared in a manner known per se in the art and their detergency, foamability, bactericidal effects and anti-dandruff properties were evaluated. The results are shown in Tables 1–3.

(Evaluation Method)

Detergency: After 20 g of a hair bundle (15 cm) of a healthy Japanese woman were coated with 1 g of a shampoo solution, they were rinsed for one minute. The touch feeling after rinsing was evaluated in accordance with the following standards by a panel consisting of 20 experts.

A: very good (at least 90% of the experts evaluated that the detergency was good)

B: good (at least 80% but smaller than 90% of the experts evaluated that the detergency was good)

C: slightly inferior (at least 70% but smaller than 80% of the experts evaluated that the detergency was good)

D: inferior (smaller than 70% of the experts evaluated that the detergency was good).

Foamability: Into a cylinder, 800 ml of a 20-fold diluted aqueous solution of a shampoo solution (liquid temperature:

20° C.) were poured. A stirring blade was installed in the aqueous solution, followed by the rotation for 5 minutes. Then, the solution was allowed to stand for 30 seconds and the foaming condition was evaluated according to the following standards. Incidentally, the rotational speed of the stirring blade was 1000 rpm and it was reversed every 5 seconds.

A: fairly good foaming

B: good foaming

C: foaming occurs but not satisfactory

D: hardly foaming

Anti-dandruff properties: Anti-dandruff effects of each shampoo were evaluated once a day for 2 weeks by a panel consisting of 10 experts.

A: at least 9 experts feel a decrease in dandruff.

B: 8 experts feel a decrease in dandruff.

C: 7 experts feel a decrease in dandruff

D: 6 experts or less feel a decrease in dandruff.

The test on bactericidal effects was carried out by forming a dilution system of each component, inoculating bacteria to be tested (*Staphylococcus aureus* IFO 12732, *Escherichia coli* IFO 3972, *Malassezia furfur* IFO (658)), and determining the concentration and time at which 100% of the bacteria were destroyed. Described specifically, 0.1 ml of bacteria (about $10^9$–$10^{10}$ cell/ml) precultured using an SCD medium (product of Nippon Seiyaku Co., Ltd.) for *S. aureus* or *E. coli*, or Molt-Yeast medium ["Casjtone", trade name; product of Difco: 0.5%, Yeast-extract (product of Difco): 0.67%, Yeast-Nitrogen-base (product of Difco): 0.5%, glucose: 2% and "Reodol TW-S120" (trade name; product of Kao Corporation: 0.1%] for *M. furfur* was weighed, to which 10 ml of a solution which has been diluted with sterilized distilled water to a predetermined concentration (bactericide concentration of 1, 5, 10, 25, 50, 75, 100, 200, 300 or 500 ppm) were inoculated to act on the bacteria at room temperature. One inoculating loopful of the solution contacted with the bacteria was weighed at fixed intervals (5, 10, 15, 30 minutes), followed by the inoculation to a micro Petri dish ("96-Cell Wells", product of CORNING) containing 0.3 ml of a postculture medium. The bacteria were cultured at 30° C. for 3 days. The growth of the bacteria was macroscopically observed and the strength of the effects were judged by a number of areas sterilized. Described specifically, the judgement was conducted by counting the number of the areas on the micro planter where growth of the bacteria was not observed (40 at maximum).

TABLE 1

(wt. %)

| | Invention Products | | | | | |
|---|---|---|---|---|---|---|
| | 1 | 2 | 3 | 4 | 5 | 6 |
| Sodium polyoxyethylene lauryl ether sulfate (EO = 3) | 10 | 10 | 10 | 10 | 10 | 10 |
| Polyoxyethylene lauryl ether sulfate triethanolamine salt (EO = 3) | | | | | | |
| Lauric acid amidopropyl-betaine | | 3 | | | | |
| Laurylhydroxy- | | | 3 | | | |

TABLE 1-continued (wt. %)

| | Invention Products | | | | | |
|---|---|---|---|---|---|---|
| | 1 | 2 | 3 | 4 | 5 | 6 |
| sulfobetaine | | | | | | |
| Lauryldimethyl-amine oxide | | | 3 | 3 | | |
| Lauroyldi-ethanolamide | | | | 1 | | 2 |
| Lauroylmono-ethanolamide | 1 | 1 | 1 | | 2 | |
| Benzalconium chloride * | 0.5 | 0.5 | 0.5 | 0.5 | 0.5 | 0.5 |
| Disodium ethylene diamine tetra-acetate | 0.54 | 0.54 | 0.54 | 0.54 | 0.54 | 0.54 |
| Disodium succinate | | | | | | |
| Water | Balance | Balance | Balance | Balance | Balance | Balance |
| Detergency | A | A | A | A | A | A |
| Foamability | A | B | B | A | A | A |
| Anti-dandruff properties | A | A | A | A | B | B |
| Effects against *S. aureus* (the number of sterilized areas) | 25 | 24 | 25 | 28 | 22 | 21 |
| Effects against *E. coli* (the number of sterilized areas) | 31 | 32 | 35 | 36 | 28 | 27 |
| Effects against *M. furfur* (the number of sterilized areas) | 25 | 25 | 26 | 27 | 22 | 20 |

*Alkyl composition: $C_{12}/C_{14}$ = 50/50 (weight ratio) (which can be also be applied to the following examples)

TABLE 2

(wt. %)

| | Inventive Products | | | Comparative products | |
|---|---|---|---|---|---|
| | 7 | 8 | 9 | 1 | 2 |
| Sodium polyoxyethylene lauryl ether sulfate (EO = 3) | 10 | | 10 | 10 | 10 |
| Polyoxyethylene lauryl ether sulfate triethanolamine salt (EO = 3) | | 10 | | | |
| Lauric acid amidopropyl-betaine | | | | | |
| Laurylhydroxy-sulfobetaine | | 3 | 3 | | 3 |
| Lauryldimethyl-amine oxide | 2 | | | | |
| Lauroyldi-ethanolamide | | | | | |
| Lauroylmono-ethanolamide | | 1 | 1 | | 1 |
| Benzalconium chloride * | 0.5 | 0.5 | 0.5 | 0.5 | |
| Disodium ethylene diamine | 0.54 | 0.54 | | 0.54 | 0.54 |

TABLE 2-continued

|  | Inventive Products | | | Comparative products | | (wt. %) |
| --- | --- | --- | --- | --- | --- | --- |
|  | 7 | 8 | 9 | 1 | 2 | |
| tetra-acetate | | | | | | |
| Disodium succinate | | | 0.38 | | | |
| Water | Balance | Balance | Balance | Balance | Balance | |
| Detergency | A | A | A | A | A | |
| Foamability | A | A | A | B | A | |
| Anti-dandruff properties | B | A | A | C | D | |
| Effects against S. aureus (the number of sterilized areas) | 25 | 30 | 25 | 0 | 0 | |
| Effects against E. coli (the number of sterilized areas) | 27 | 36 | 29 | 20 | 0 | |
| Effects against M. furfur (the number of sterilized areas) | 21 | 28 | 24 | 5 | 0 | |

Example 2

(Shampoo)

A shampoo having the below-described composition was prepared in a manner known per se in the art.

| Polyoxyethylene lauryl ether sulfate triethanolamine salt (EO = 3) | 10% |
| --- | --- |
| Lauroyldiethanolamide | 2% |
| Lauryldimethylamine oxide | 2% |
| Laurylhydroxysulfobetaine | 1% |
| Lauric acid | 0.5% |
| Benzethonium chloride | 0.5% |
| Disodium ethylene diamine tetraacetate | 0.54% |
| 89% Triethanolamine | 2.4% |
| Perfume | trace |
| Purified water | balance |

The shampoo so obtained had excellent detergency and foamability and at the same time had high anti-dandruff effects.

Example 3

A shampoo having the below-described composition was prepared in a manner known per se in the art.

| Polyoxyethylene lauryl ether sulfate sodium salt (EO = 3) | 10% |
| --- | --- |
| Lauric acid monoethanolamide | 1% |
| Lauryl amidopropylbetaine | 2% |
| Laurylhydroxysulfobetaine | 3% |
| Potassium laurate | 0.5% |
| Benzethonium chloride* | 0.5% |
| Disodium succinate | 0.38% |
| Chlorohexidine gluconate | 0.19% |
| Perfume | trace |
| Purified water | balance |

The shampoo so obtained had excellent detergency and foamability and at the same time had high anti-dandruff effects.

Example 4

(Body Shampoo)

A body shampoo having the below-described composition was prepared in a manner known per se in the art.

| Polyoxyethylene lauryl ether sulfate sodium salt (EO = 3) | 10% |
| --- | --- |
| Lauroyl monoethanolamide | 1% |
| Lauric acid amidopropylbetaine | 2% |
| Laurylhydroxysulfobetaine | 3% |
| Benzethonium chloride* | 1% |
| Disodium succinate | 0.76% |
| Perfume | trace |
| Purified water | balance |

The body shampoo so obtained had excellent detergency and foamability and at the same time had excellent antipruritic and deodorizing effects.

Example 5

(Shampoo)

A shampoo having the below-described composition was prepared in a manner known per se in the art.

| Polyoxyethylene lauryl ether sulfate sodium salt (EO = 3) | 18% |
| --- | --- |
| Coconut fatty acid diethanolamide | 1% |
| Sodium cocoamphoacetate | 0.8% |
| Benzethonium chloride* | 1% |
| Disodium succinate | 0.45% |
| Sorbitol | 2% |
| Perfume | trace |
| Purified water | balance |

The body shampoo so obtained had excellent detergency and foamability and at the same time had excellent anti-dandruff effects.

Example 6

(Shampoo)

A shampoo having the below-described composition was prepared in a manner known per se in the art.

| Polyoxyethylene lauryl ether sulfate sodium salt (EO = 3) | 22% |
| --- | --- |
| Coconut fatty acid monoethanolamide | 0.8% |
| Lauryl dimethylamine oxide | 0.8% |
| Benzalkonium chloride* | 1.5% |
| Disodium succinate | 0.7% |
| Sorbitol | 2% |
| Perfume | trace |
| Purified water | balance |

The shampoo so obtained had excellent detergency and foamability and at the same time had excellent anti-dandruff effects.

What is claimed is:

1. A detergent composition comprising the following components (A), (B), (C) and (D):

(A) from 8 to 25 wt. % of a sulfate ester surfactant represented by the following formula (1):

$$R^1O-(CH_2CH_2O)_n-SO_3M^1 \qquad (1)$$

wherein $R^1$ represents a linear or branched $C_{8-20}$ alkyl or alkenyl group, n stands for an integer of 0–10 on average, and $M^1$ represents an alkali metal atom, alkaline earth metal atom, ammonium salt, alkyl ammonium salt or alkanol ammonium salt;

(B) from 0.5 to 10 wt. % of at least one surfactant selected from the group consisting of amphoteric surfactants, amine oxide surfactants, alkanol amide surfactants and amide amino-acid surfactants;

(C) from 0.2 to 5 wt. % of at least one cationic bactericide selected from the group consisting of cationic bactericides represented by the below-described formulas (3), (4) and (5), respectively and polyhexamethylene biguanide:

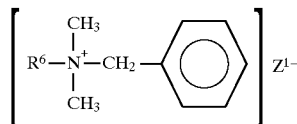   (3)

wherein $R^6$ represents a $C_{8-14}$ hydrocarbon group or a group represented by the following formula:

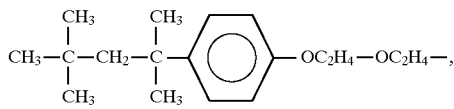

$Z^1$ represents a halogen atom, an amino acid, a fatty acid, an anionic residue of a phosphate ester, phosphonate ester or sulfate ester having a linear or branched $C_{1-30}$ alkyl or alkenyl group, or an anionic oligomer or polymer containing a formalin condensate of a sulfonated polycyclic aromatic compound which may contain styrenesulfonic acid having a polymerization degree of at least 3 or may contain as a substituent a hydrocarbon group;

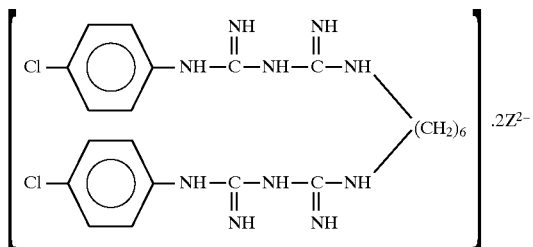   (4)

wherein $Z^2$ represents a gluconic acid, acetic acid or hydrochloric acid;

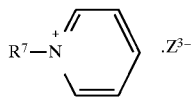   (5)

wherein $R^7$ represents a linear or branched $C_{6-18}$ alkyl group, and $Z^3$ represents a halogen atom, an amino acid, a fatty acid, an anionic residue of a phosphate ester, phosphonate ester, sulfonate ester or sulfate ester having a linear or branched $C_{1-30}$ alkyl or alkenyl group, or an anionic oligomer or polymer containing a formalin condensate of a sulfonated polycyclic aromatic compound which may contain styrenesulfonic acid having a polymerization degree of at least 3 or may contain as a substituent a hydrocarbon group; and (D) a metal chelating agent, the weight ratio of the component (A) to the component (B) falling within a range of from 1 to 50.

2. A detergent composition according to claim 1, wherein the weight ratio of (A) to (B) falls within a range of from 1 to 10.

3. A detergent composition according to claim 1, wherein the weight ratio of (A) to (B) falls within a range of from 1 to 6.

4. A detergent composition according to claim 1, wherein the molar ratio of (D):(C) is 0.5–5:1.

5. A detergent composition according to claim 2, wherein the molar ratio of (D):(C) is 0.5–5:1.

6. A detergent composition according to claim 3, wherein the molar ratio of (D):(C) is 0.5–5:1.

7. A detergent composition according to claim 1, wherein the metal chelating agent (D) is at least one material selected from the group consisting of ethylene diamine tetraacetic acid, succinic acid, salicylic acid, oxalic acid, lactic acid, fumaric acid, tartaric acid and 1-hydroxyethane-1, 1-diphosphonic acid and salts thereof.

8. A detergent composition according to claim 2, wherein the metal chelating agent (D) is at least one material selected from the group consisting of ethylene diamine tetraacetic acid, succinic acid, salicylic acid, oxalic acid, lactic acid, fumaric acid, tartaric acid and 1-hydroxyethane-1, 1-diphosphonic acid and salts thereof.

9. A detergent composition according to claim 3, wherein the metal chelating agent (D) is at least one material selected from the group consisting of ethylene diamine tetraacetic acid, succinic acid, salicylic acid, oxalic acid, lactic acid, fumaric acid, tartaric acid and 1-hydroxyethane-1, 1-diphosphonic acid and salts thereof.

10. A detergent composition according to claim 4, wherein the metal chelating agent (D) is at least one material selected from the group consisting of ethylene diamine tetraacetic acid, succinic acid, salicylic acid, oxalic acid, lactic acid, fumaric acid, tartaric acid and 1-hydroxyethane-1, 1-diphosphonic acid and salts thereof.

11. A detergent composition according to claim 5, wherein the metal chelating agent (D) is at least one material selected from the group consisting of ethylene diamine tetraacetic acid, succinic acid, salicylic acid, oxalic acid, lactic acid, fumaric acid, tartaric acid and 1-hydroxyethane-1, 1-diphosphonic acid and salts thereof.

12. A detergent composition according to claim 6, wherein the metal chelating agent (D) is at least one material selected from the group consisting of ethylene diamine tetraacetic acid, succinic acid, salicylic acid, oxalic acid, lactic acid, fumaric acid, tartaric acid and 1-hydroxyethane-1, 1-diphosphonic acid and salts thereof.

13. A detergent composition according to claim 1, wherein the surfactant of component (B) is one or more surfactants selected from the group consisting of lauric acid amidopropylbetaine, laurylhydroxysulfobetaine, lauryldimethylamine oxide, lauroyldiethanolamide, and lauroylmonoethanolamide.

* * * * *

UNITED STATES PATENT AND TRADEMARK OFFICE
CERTIFICATE OF CORRECTION

PATENT NO. : 5,858,936

DATED : January 12, 1999

INVENTOR(S): Yoshinori Tamura, et al.

It is certified that an error appears in the above-identified patent and that said Letters Patent is hereby corrected as shown below:

Column 13, Line 29 "phosphonate ester or" should read --phosphonate ester, sulfonate ester or--.

Signed and Sealed this

Twenty-first Day of September, 1999

Attest:

Q. TODD DICKINSON

Attesting Officer

Acting Commissioner of Patents and Trademarks